(12) United States Patent
Unsworth

(10) Patent No.: US 6,520,927 B1
(45) Date of Patent: Feb. 18, 2003

(54) METHOD AND DEVICE TO PREVENT CARDIAC DYSRHYTHMIAS

(76) Inventor: John D. Unsworth, 365 Lodor St., Ancaster, Ontario (CA), L9G225

( * ) Notice: Subject to any disclaimer, the term of this patent is extended or adjusted under 35 U.S.C. 154(b) by 0 days.

(21) Appl. No.: 09/482,865

(22) Filed: Jan. 14, 2000

(51) Int. Cl.$^7$ ............................................. A61N 1/30
(52) U.S. Cl. ....................... 604/19; 604/508; 604/511; 128/898
(58) Field of Search ..................... 604/19, 500, 506, 604/507, 508, 511; 128/898; 606/1

(56) References Cited

U.S. PATENT DOCUMENTS

| | | |
|---|---|---|
| 4,159,659 A | 7/1979 | Nightinegle |
| 4,204,438 A | 5/1980 | Binaris |
| 4,286,599 A | 9/1981 | Hahn |
| 4,771,660 A | 9/1988 | Yacowitz |
| 5,054,339 A | 10/1991 | Yasowitz |
| 5,219,358 A | 6/1993 | Bendel |
| 5,401,242 A | 3/1995 | Yasowitz |
| 5,863,241 A | 1/1999 | Schaer |
| 6,016,809 A | * 1/2000 | Mulier et al. ................ 128/898 |
| 6,047,700 A | * 4/2000 | Eggers et al. ................ 128/898 |
| 6,053,172 A | * 4/2000 | Hovda et al. ................ 128/898 |
| 6,063,079 A | * 5/2000 | Hovda et al. ................ 128/898 |
| 6,086,585 A | * 7/2000 | Hovda et al. ................ 128/898 |
| 6,109,268 A | * 8/2000 | Thapliyal et al. ........... 128/898 |
| 6,159,208 A | * 12/2000 | Hovda et al. ................ 128/898 |
| 6,179,824 B1 | * 1/2001 | Eggers et al. ................ 604/500 |
| 6,190,370 B1 | * 2/2001 | Tsui ............................ 604/508 |
| 6,203,542 B1 | * 3/2001 | Ellsberry et al. ........... 128/898 |
| 6,309,387 B1 | * 10/2001 | Eggers et al. ................ 128/898 |

FOREIGN PATENT DOCUMENTS

WO     95/15115     6/1995

* cited by examiner

Primary Examiner—Teresa Walberg
Assistant Examiner—Fadi H. Dahbour

(57) ABSTRACT

A method and to treat dysrhythmias of the heart, for example atrial fibrillation, by creating artificial conduction pathways, fields or patterns. These artificial pathways or fields are created by injecting materials having desired electrical properties into the walls of the heart.

2 Claims, 3 Drawing Sheets

METHOD AND DEVICE TO PREVENT CARDIAC DYSRHYTHMIAS

FIELD OF THE INVENTION

This invention generally relates to the conduction system of the heart and the creation of artificial lines of conduction in the wall of the heart to reduce or eliminate cardiac dysrhythmias, for example atrial fibrillation and also to conduct normal impulses from the senatorial node to avoid the necessity of implanting an artificial pacemaker.

INTRODUCTION AND SUMMARY OF THE INVENTION

The conduction system of the normal heart involves impulse formation at the sinus node and impulse propagation through the rest of the heart. Automaticity, or the property of generating spontaneous depolarization to threshold, enables the SA and AV nodes to generate cardiac action potentials without any stimulus. Automaticity is also present in the left atrium and is thought to contribute to the cause of atrial fibrillation.

The SA node sets the pace because normally it has the fastest rate, which is why it is called the natural pacemaker of the heart. The impulse propagates from the SA note to the AV node and from there to the bundle of His (atrioventricular bundle, common bundle) and finally through the bundle branches of the interventricular septum to Purkinje fibers in the heart wall.

Failure of conduction along the pathways can cause various pathologies. A failure of conduction between the sinus node and the atrium will result in the arrhythmia known as SA block. Failure of conduction can also occur at the level of the connection between the atrium and ventricle. This would produce arrhythmias known as AV block. Establishment of a conduction pathway between these sites should prevent these forms of arrhythmias. This invention provides a means and method for creating conduction pathways between these sites to prevent AV and SA block.

Atrial fibrillation may be caused in part by the failure (partly or totally) of conduction from the AV node to the left atrium. This would reduce the regulating effect of the AV node impulse on the left atrium and leave the areas of automaticity in the left atrium to initiate impulses independently of AV regulation, or in competition with residual AV impulses. The establishment of a conduction pathway from the AV node to the left atrium may prevent atrial fibrillation without recourse to ablative surgery and the implantation of artificial pacemakers. This invention provides a method and a means to provide artificial conduction pathways between these sites. This method would address the cause of fibrillation more directly than present methods.

Another approach to treating atrial fibrillation would be to create a network of pathways, for example in a grid pattern, that would in effect short circuit the impulses or isolate them into small areas, before they are able to propagate sufficiently to cause fibrillation. This grid pattern would be imparted into the walls of the fibrillating atria. Another pattern might be an array of spiral patterns that would act as a capacitor and dissipate the unwanted impulses. These spiral patterns could be connected to each other or disconnected or some of both. Interleaved X's or spider patters might also be effective.

Conduction through the tissue can also be affected by the orientation of cells forming the tissue. The cells favour transmission in a direction that follows the line joining the gap junctions between the cells and this can cause the impulse to travel through the heart muscle at different rates and in diverging directions. If these impulse fronts later merge or "reenter", from different directions they cause the tissue fibrillate. The establishment of conduction pathways that would even-out the speed of the impulse front through the heart tissues should reduce fibrillation due to reentry. Angina might also be treated by establishing conduction pathways in the walls of the hears where angina pain is experienced.

What is needed then is a method to create conduction pathways between various parts of the heart. Conduction pathways generally being lines or fields along which or through which conduction is favoured or modified.

The use of carbon as a means of reducing resistance of the skin tissue to electrical impulses by tattooing carbon into the skin tissue for the purpose of attaching diagnostic sensors was described by S. A. Hoenig, P. L. Gildenberg and K. S. Krishna Murthy, *Generation of Permanent, Dry, Electrical Contacts by Tatooing Carbon into Skin Tissue*, IEEE Transactions on Biomedical Engineering, Vol. BME-25, No. 4, July 1978, Pages 380–382. The carbon with fluid carrier was injected into the skin with a syringe having a standard hollow needle. It was found that this method produced better results that standard reciprocating tattoo electrical appliances.

What has not been appreciated until now is that the hearts conductive system can be selectively modified by impregnating materials that impart particular electrical properties to the tissue. This approach will essentially rewire the heart.

Pathways or fields of conduction can best be created by impregnating the tissue with materials that enhance the particular electrical properties being sought. In most cases what will be sought is greater conduction; but in other cases greater impedance or insulation may be sought.

The location of the pathways that are most beneficial will depend upon the electrophysiology of the particular heart being treated. As three dimensional imaging becomes more refined, the conductance pathways of a heart may be studied in greater detail and more sophisticated strategies developed to alter and improve these preexisting pathways with artificial pathways that are described in this invention.

The artificial conduction pathways that are the subject of this patent can be applied by different methods depending on the location and pattern of the pathways that the surgeon wishes to create. Open heart surgery will give the surgeon the most flexibility in applying the pathways and if open heart surgery is necessary due to the location of the pathways required, a simple syringe will be suitable for most cases. In other cases the paths can be applied with a automated syringe that is described in this patent and forms a part of this invention. This hand-held automated syringe can apply any pattern to the inner or outer surface of the walls of the heart, although in most cases the inner pathways will be created on the inside of the heart. While tattooing instruments exist such as those described in U.S. Pat. No. 5,401,242 of Dr. Harold Yacowitz, the existing systems do not permit real-time adjustments in needle depth, amount of material delivered, or changes in the part of the stroke that material is delivered. The automated syringe that is a preferred embodiment of this invention can produce conductive tracts of varying depth, varying densities of material deposited, all without stopping to adjust the instrument. No other system can do all these things.

If a syringe is used, the pathway of conductive materials can be applied by a number of insertions with concomitant injections of a desired amount of conductive material. This series of injections can form a pathway or field, depending upon what is required at various depths in the tissue. This method would be similar to tattoo methods, except that it is not automated, but allows for more control of the pattern of the pathway and field, its extent and depth at various points. This methods would be used of creating conduction pathways close to the surface of the interior heart walls.

The second method of applying a pathway to the heart tissue would be more direct and involve creating an approximately continuous ribbon of conduction material. This would involve inserting the syringe, usually a relatively long distance, and injecting the conducting material while inserting the needle or withdrawing it, or both. The conductive material can be continuous or discontinuous, depending upon what is required. This would be controlled by the surgeon's application of the syringe plunger, or activation of a pump. This method typically would be used for establishing a conduction pathway at greater depths than the first method described above; for example, from the Sinoatrial node (SA) to the left atrium. For many operations, a combination of both methods might also be required.

For some operations it might be preferable to enter the heart through the lumens of arteries and veins connected to the heart. These methods are well known to the art. A catheter delivered to the heart by these methods could have a distal end that injects the conducting material into the heart tissue by various means. The simplest method would be a long syringe needle that would extend out of a hole at or near the distal end of the said catheter. The distal end of the said catheter needle can be straight or hooked, depending upon what is required. If straight, it would simply exit out of the distal end of the catheter, the lumen of which encloses the needle. If hooked it could be made of superlastic nitinol that would permit it to be straight in the catheter, but rebound into a curved shape as it exits the hole of the side of the catheter. A straight syringe needle would apply straight ahead injections and the curved syringe needle would apply injections along the side of the longitudinal axis of the distal end of the catheter. A catheter could of course accommodate a number of syringe needles to speed the application of the track or pattern. These could exit, bundled together, out of one hole or out of separate holes. If a curved needle is used, means for aligning the distal needle tip with the hole in the side of the catheter through which it must pass, must be provided. This could be a simple ridge placed longitudinally along the distal portion of the needle that would register with a groove running along the longitudinal axis of the wall of the distal end of the catheter. Other means well known to the art could also be used to align the curving needle to ensure that it exits at the hole properly.

A preferred embodiment of the invention for the delivery of the material is an automated syringe and catheter system. The curved and straight needle could of course be automated and have an automated pump that would pulse at the same time the needle was inserted into the tissue. This would require that the either or both the needle and the interior walls forming the lumen of the catheter be insulated, by for example Teflon. The needle would then change its impedance when it entered the tissue of the heart and material would not be pumped unless the capacitance was such that the needle must be in the tissue. This would prevent material from mixing in with the blood of the heart. This pulse of the pump could be programmed by computer means to also vary the amount of material delivered at each part of the stroke. For example it might be important to have more material ejected at the end of a stroke, while in other cases it might be important to have it ejected evenly from the point of entry to the end of the throw of the needle's back an forth motion. It is also important to vary the depth stroke of the needle into the tissue. The conduction track required might vary in depth along the interior wall of the heart, it is therefore important to be able to vary the depth that the needle can penetrate. This can be accomplished by controlling the servo motor that drives the needle by computer means. It is also important to know when the needle is about to leave the hole in the distal end of the catheter and when it returns and is fully sheathed by the catheter as well as the length the needle has extended from the hole in the delivery catheter. Again this can be done by providing a series of contact points with a known and different resistances at the distal end of the needle that will make contact with a contact point on the distal end of the delivery catheter. The relative position of the tip of the needle and the hole of the catheter can then be determined by detecting the resistance in the circuit formed by the catheter and needle through the various contact points, such detection takes place outside the body and this information is reported to the computer which controls the motion of the needle and the pump. This will ensure that the needle's position is known to the computer during the procedure. Other positional detection means are well known to the art, such as linear induction measuring devices, but these are all well known to the art and other preferred embodiment could incorporate these means. Because the needle must be somewhat loose in the lumen of the catheter to permit movement, it is unreliable to measure the relative positions of the distal needle tip and said hole from outside the body. As can be readily appreciated this method of delivery is quite different from that described in U.S. Pat. No. 5,401,242 of Dr. Harold Yacowitz. The computer controlled servo motor and servo pump allow for on-the-fly control of needle stroke, speed of stroke and amount of material deposited at each part of the stroke. These parameters can be varied as the operation is being conducted, even at every stroke of the needle. The tissue insertion detection means also ensures that no material is deposited in the blood stream and also allows for a variation in the separation between the catheter and the heart wall into which the needle in injected.

The preferred material for impregnation are particles or molecules of carbon 60, or other forms of carbon including activated carbon, and other organic materials, such as conductive plastics, that are conductive and that are at the same time biologically compatible with the heart muscle. Other preferred materials are particles of any inorganic conductive material that is biologically compatible, for example iron, stainless steel, nickel titanium (nitinol) and oxides of these metals. However, Carbon 60 is thought to be the best material as it is relatively inert, conductive and has high lubricity which would minimize irritation from the movement of the heart muscle. Other forms of carbon, iron and iron oxide are the principal other preferred materials due to their conductivity and bio-compatability. Radio-opaque dies can be added to the material to be impregnated to allow the surgeon to view the progress of the operation. If these materials are applied with a syringe or similar device, they will be suspended or dissolved in a carrier fluid such as saline water, or other suitable carrier fluid used in other pharmacological preparations.

Rather than injecting carbon materials into the tissue, the tissue itself could be carbonized by the application of photo-thermal energy to the tissue. This preferred embodiment of the invention would involve the delivery of the photo-thermal energy, preferably produced by a laser, delivered directly or particularly in the case of an interluminal operation, down an optical fibre to the area of the heart wall that requires carbonization. An infrared or near infrared laser would probably be best for carbonization, but other frequencies would also be suitable. It may be beneficial to use one laser frequency to produce the holes and another to carbonize the lumen of the hole so formed. In this case a tunable laser might be utilized or two lasers optically linked by means well known to the art. The optical fibre would be of such a diameter and the laser pulses of such energy to produce holes of desired diameter and depth to effect the purpose. In some cases holes would not be required in which case surface and near surface carbonization could be effected by using lower energies. Using this method the electrical impulse of the heart need not travel down the axis of an individual tract or hole, but depending upon the depth of the holes and the arrangement of the array of holes, the electrical impulse could travel normal to the axis of the holes. Additional carbon or conductive material could also be introduced into the holes so created to further increase the conductivity of the heart wall.

Another preferred embodiment would be an optical fibre within the lumen of a catheter, the distal end of the catheter being sufficiently sharp to permit it to be pushed through the heart wall and an opening at or near the distal end, to permit the delivery of photo-thermal energy to the adjoining tissue through which the catheter is advanced or retreated. This catheter could be of the steerable or non-steerable type. A device of this type could be advanced through the walls of the heart, and then the carbonizing laser could be turned on while the optical fibre delivery device is pulled back. This would ensure that the position of the tract is correct before the tract is carbonized.

As referred to above, insulating materials, such insulating plastics or ceramic materials could be injected to increase the resistance of the tissues to the passage of the electrical impulse through the tissue. This approach is similar to the ablative surgery approach where the tissue is imparted with higher resistance by cauterizing the tissue. This method of injecting biologically compatible insulating materials would however be much less traumatic. These tracks would in most cases be the same in direction and orientation as the ablative tracts created by conventional means.

Alternatively materials with a high capacitance might be used. This would act as a capacitor smoothing out the pulse and bringing it below the threshold at which it would cause the heart muscle to fibrillate. Materials of this sort could be made from biologically compatible metals with biologically compatible oxide or insulative surfaces such as a ceramic or plastic. As mentioned above, patterns of conductive materials could also create areas of high capacitance.

All three methods, that is tracts of higher conductance, tracts of insulative barriers and tracts of higher capacitance or a combination of two or more of the following, could all be injected into the heart wall be the means described above.

While the method is described mainly in the context of reducing fibrillation, AV and SA block, it should be appreciated that this method allows one to change the electrical properties of the heart for other purposes. For example, heart pace makers could be made more effective and durable if conductive tattoos were impregnated into the tissue of the heart using the methods described. Using such methods pacemakers might be introduced into the patient's vascular system, e.g. the femoral vein, percutaneously or by way of a cut-down, advanced therein into the heart and implanted into the heart with electrodes tattooed in the heart walls.

DESCRIPTION OF THE DRAWINGS

These and other features, aspects and advantages of the present invention will become better understood with reference to the following description, appended claims and accompanying drawings where:

FIG. 1 also shows input means 8 (joy stick) and reporting means 9 (computer screen) for the operator.

FIG. 2 is a drawing of the distal end of the needle 4 in the delivery catheter 5, enclosed in a sheath 10. FIG. 2 illustrates the needle deflecting from its straight shape 4 to its curved end shape 4a and projecting through an opening 11 in the delivery catheter 5 and the larger opening 14 in the sheath 10.

DESCRIPTION OF PREFERRED EMBODIMENTS

Figure 1:
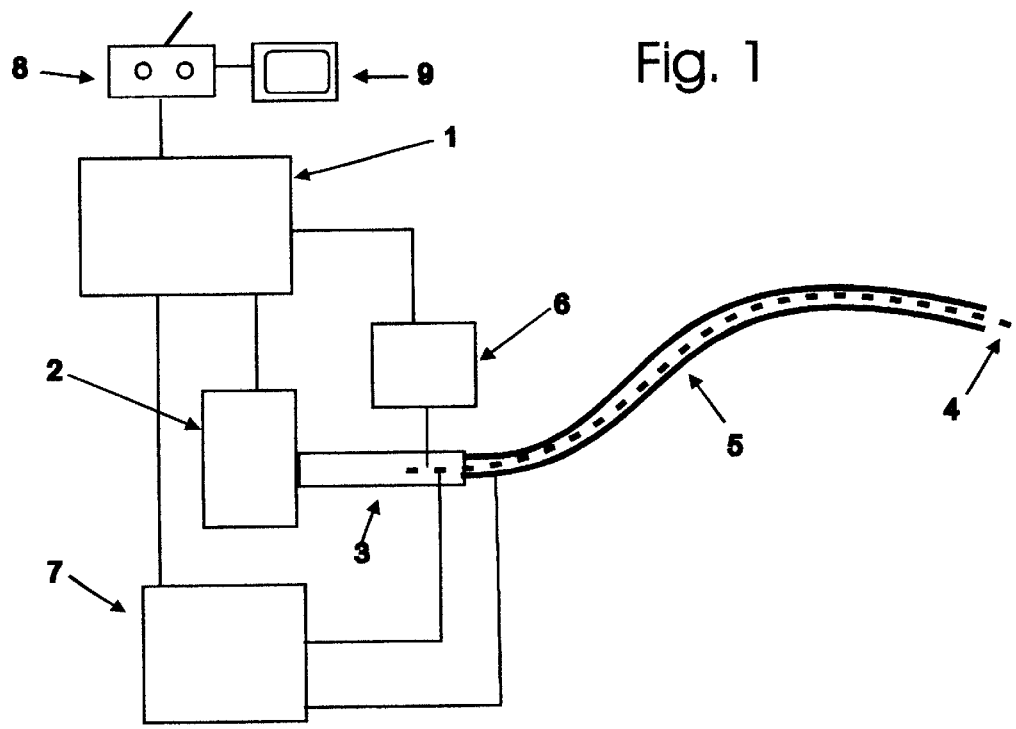
FIG. 1 is a drawing of the basic system illustrating the computer controller 1 controlling a servo motor 2 and linear drive 3 that moves the needle 4 back and forth in the delivery catheter 5, as well as the servo driven and computer controlled peristaltic metering pump 6, and detection means 7 for the position of the needle in the delivery catheter and for determining when the needle is in the heart tissue, such detection means reporting to the computer 1.

A preferred embodiment of the means for practicing the method, together comprising the invention that is shown on FIG. 1 and including as its main elements a controlling computer 1 which controls the motion of a needle 4 by means of a servo or other suitable motor 2 which in turn is linked to a linear screw drive 3, or other suitable linear drive. The computer 1 controls the back an forth motion of the needle 4 which is detachable attached at its proximal end to the moving carriage in the linear drive. Since the needle is computer controlled, the stroke of the needle can be controlled by the operator moving the joystick located on the input means 8 all in real-time. The speed of the needle during all phases of the stroke and the distance the needle is moved back and forth are all within the immediate control of the operator or subject to preprogrammed sequences or selectable routines. Also the start position of the needle 4 relative to the delivery catheter 5 can be set. This permits the surgeon to create a conductive pathway that can have varying depths from the surface of the tissue. The needle 4 is of course hollow to permit the desired material to be pumped by pump 6 to the distal end of the needle for injection into the body tissue. The end of the needle 6 can be any standard syringe needle type including the standard bevel, blunt or side-ejecting with solid point end.

The delivery catheter 5 is detachable attached at its proximal end to the stationary case of the linear drive 3.

The sheath 10 is not shown in FIG. 1 for diagrammatic clarity. A servo driven peristaltic metering pump 6 pumps material that has certain electrical properties together with a fluid carrier from a reservoir in 6 to the needle 4. The reservoir could of course contain a number of different materials that the pump could select as instructed by the computer 1. There would also be a flushing routine that would evacuate the needle 4 of the previous material used and ready it for the next selected material. Various connecting means, all well known to the art can be used to connect the delivery line from the pump to the needle 4. The said servo driven pump is controlled by computer 1 which pumps said material into the needle at precise times and precise amounts as the distal end of the needle 4 is inserted and withdrawn from the body tissue into which it is inserted. The computer coordinates the amount of said material delivered with the motion of the needle which is driven by the said linear drive 3. The amount of material supplied by the pump 6 to the needle 4 can vary during the stroke as instructed by the computer 1.

Figure 2:
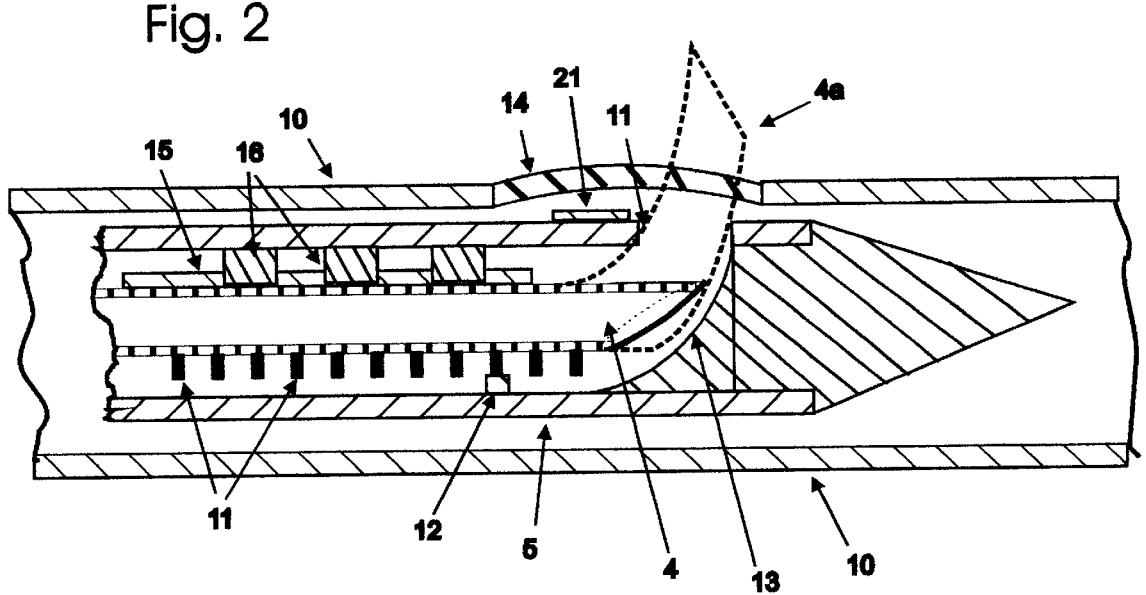
FIG. 2 is a drawing of the side acting automated syringe.

Detection means 7 detects the resistance in the circuit formed by the needle 4 and delivery catheter 5 through the junction formed by the contact between resistors 11 and contact pad 12 shown on FIG. 2. Since each of the resisters has a different resistance, which is known by the computer program in computer 1, the relative location of the distal end of the needle 4 in delivery catheter 5 will be known to the computer 1. While this description of a preferred embodiment of the invention uses this means to detect and report the position of the needle 4 and delivery catheter 5, it should be understood that other methods are well known to the art and might in certain embodiments be more convenient. Detection means 7 also detects and reports to the computer 1 the impedance of the needle 4. The impedance of needle 4 will indicate when the needle has been inserted into the body tissue. This information is passed to the computer 1 which prevents the delivery of material through needle 4 until the needle has advanced into the body tissue. The point at which the needle first enters the body tissue is also reported to the computer 1 for the purpose of calculating the distance the needle must be advanced by the linear drive in order to reach a certain depth in the body tissue. Other preferred embodiments would include other means for detecting when the needle has entered body tissue and these are well known to the art and include a detector on the drive mechanism that detects when the load on the needle 4 is of such a force to indicate that it has started to enter the body tissue and when the load drops down to indicate when the needle 4 has left the body tissue.

Reporting means 9 is in most embodiments of the invention a computer screen that contains for example, a graphical representation of the distal end of the needle, the pattern of conductive material that should be applied and the location of where material has been applied and other important parameters that define the operation.

The distal end of the side acting needle is shown on FIG. 2 Sheath 10 encloses the delivery catheter 5 and the needle 4. The Sheath 10 has a long slot 14 which allows the delivery catheter 5 and needle 4, as a unit, to slide back and forth within the sheath, along the longitudinal axis of the sheath 10. This range of motion, defined by the length of slot 14, allows for a track of conductive material to be incorporated into the adjacent body tissue. This allows the delivery sheath to be pushed against a part of the interior of the heart that will cause the distal end of the sheath to bow and press the slot 14 of the sheath against the body tissue that is to be treated. The slot 14 can be of various lengths and widths.

Figure 3:
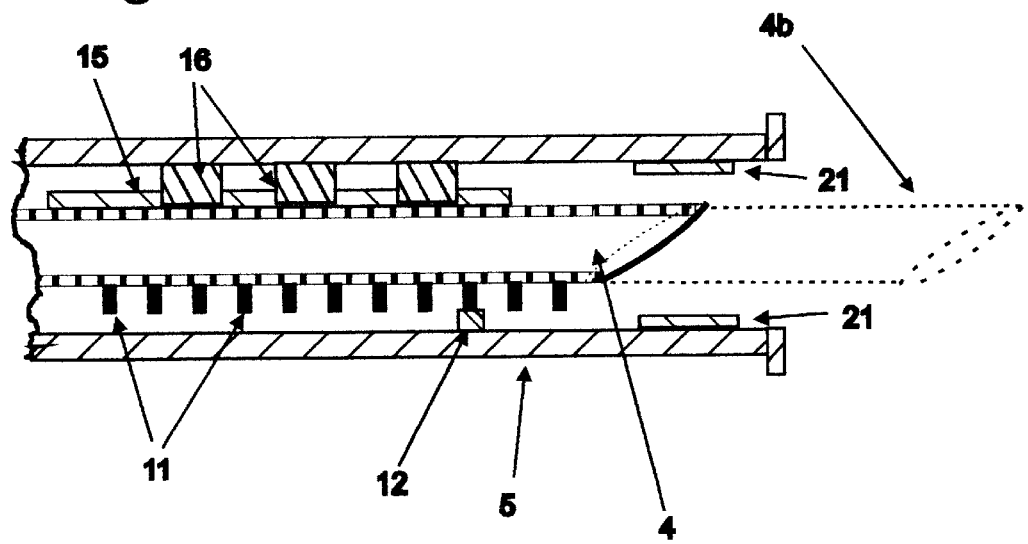
FIG. 3 is a drawing of the distal end of a forward acting automated syringe.

As the needle 4 is pushed forward by the action of the linear drive 3, it encounters ramp 13 which assists in guiding and controlling the curve of the distal end of the needle 4a and allowing it to proceed out the side of the delivery catheter through opening 11 and through the sheath through the slot 14. The distal end of the needle may have part or all of the bend already imparted into it in its unloaded state. This would help it form the desired bend without kinking at the turn. The needle 4 might be made of superlastic nickel titanium which would make it less likely to bend without kinking, but stainless steel or other materials might also be suitable. Means to align the needle and the delivery catheter are necessary to ensure that the needle bends in a predetermined way. Such means are included in a preferred embodiment in the form of a T-shaped ridge 15 running longitudinally along the distal end of the needle 4, but proximal to the part of the needle 4 that would bend when the needle is pushed out of the delivery catheter 5 to the maximum extent. This T-shaped ridge 15 slides in a T-shaped groove in guiding registers 16 located on the walls of the lumen of the delivery catheter all as shown on FIG. 2. Shown on FIG. 2 and FIG. 3 is a scavenging magnet 21. This magnet could be placed in various places other than where shown, but its purpose is to scavenge any ferrous materials that might leak out as the needle is withdrawn from the skin tissue.

FIG. 3 illustrates another preferred embodiment of the means by which conductive tracts can be created in the walls of the heart. This preferred embodiment can be hand-held or placed in the lumen of a sheath similar to that shown 10 on FIG. 2. This preferred embodiment is connected to the control system illustrated in FIG. 1 in the same way as the delivery system illustrated in FIG. 2. The needle 4 in this case does not bend, but travels in the same axis as the delivery catheter 5 and extends to 4b as illustrated. Otherwise it operates in the same manner, and has all the same capabilities as does the side acting device illustrated in FIG. 2. This device would be used in the open heart surgery to create conductive pathways.

Figure 4:
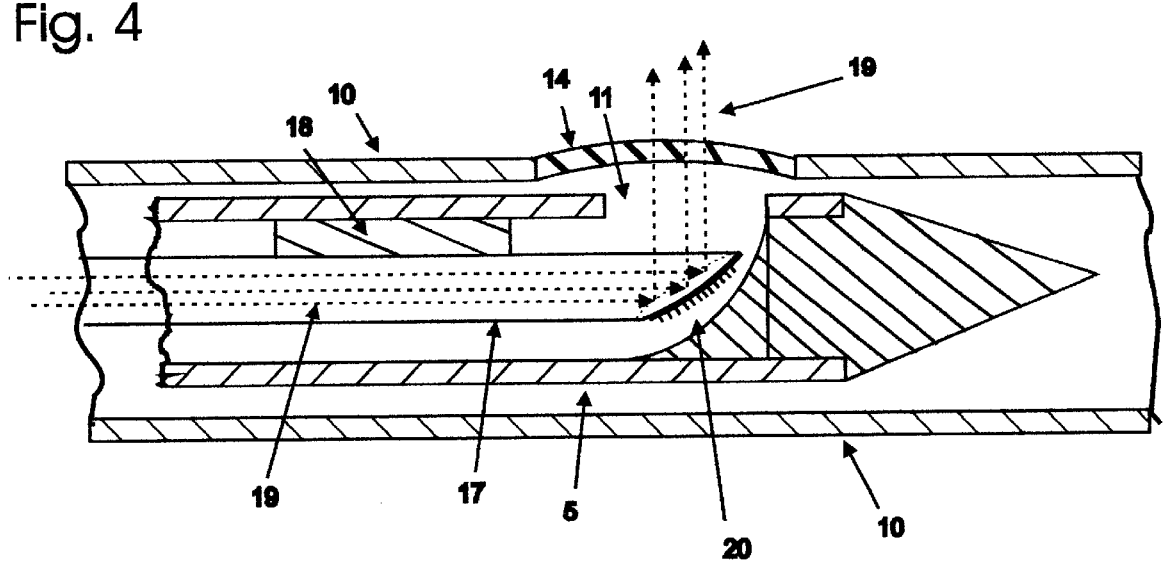
FIG. 4 is a drawing of the side firing laser system

FIG. 4 illustrates another preferred embodiment of the means by which conductive tracts can be created by carbonizing the tissue of the heart. The system illustrates a side-firing optical fiber 17 that is inside the lumen of delivery catheter 5 and held in place at the distal end by connection 18. The distal end of the optical fiber is mirrored to cause the photo-thermal energy 19 to be redirected normal to the longitudinal axis of the optical fiber and pass through the hole 11 in the delivery catheter 5 and thence through the slot 14 in the sheath and finally to the body tissue. The photo-thermal energy would be delivered to the proximal end of the optical fibre by a laser located outside the body. Other means are available to redirect the photo-thermal energy at the distal end of the optical fiber, all well known to the art, and the method shown is merely meant to illustrate one of the ways this could be accomplished. The optical fiber 17 could also project the photo-thermal energy 19 straight rather than be side-firing with a hole in the distal end of the delivery catheter 5. In order to carbonize the body tissue, a preferred embodiment of the invention uses a infrared laser but other frequencies could be used as well. As described above, holes could also be burned into the heart walls using photo-thermal energy using the device illustrated. The hole 11 and the slot 14 might be covered with a transparent material that would allow the photo-thermal energy 19 to pass through, but protect the optical fibre 17 from body fluids. In addition one or both of these holes might contain lenses to concentrate or redirect the energy as required.

Figure 5:
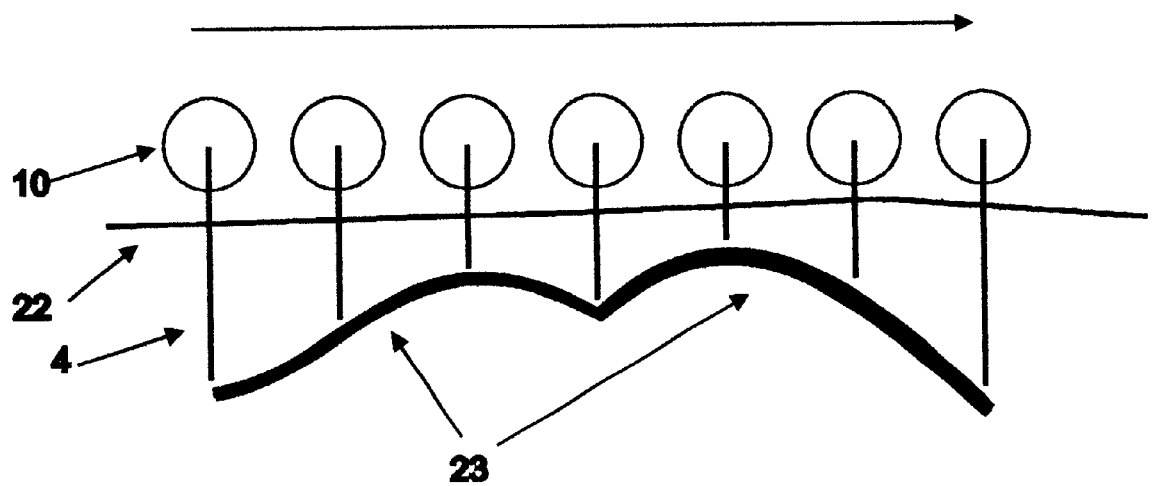
FIG. 5 is a drawing illustrating the ability of the automated syringe to create conductive pathways of varying depth from the skin surface in real time in accordance with a preprogrammed routine or on-the-fly instructions by the operator.

FIG. 5 illustrates the ability of the automated needle illustrated in FIGS. 2 and 3 to create conductive pathways of varying depth from the skin surface and of varying densities or thickness. FIG. 5 illustrates a sequence of events, running from left to right, of the fill extent of the needle's insertion on each of seven strokes. This contour can be preprogrammed into the computer 1 as a routine to be executed on a certain instruction from the operator, or it can be created on-the-fly by the surgeon using the controls 8. Also the amount of material delivered to the needle at different parts of the stroke can be varied making possible tracks of varying thickness and density, as shown on FIG. 5. No other system can do this. This gives the system the ability to create three dimensional patterns below the surface of the material that can be used to steer the electrical wave fronts and prevent reflection and reentry. These patterns can be preprogrammed into the software and the operator need only respond to cues to execute the desired pattern.

While the preferred embodiment illustrated have only one needle or one optical fibre, its is to be understood that the preferred embodiments of the invention could include two or more needles and two or more optical fibers. The use of multiple needles or fibers would increase the speed of the operation.

While this disclosure makes reference to the conduction pathways in the heart is to be understood that the methods for creating artificial conducting pathways can be applied to other parts of the body including the arteries, veins, nervous system and the brain.

While this disclosure the injection means is described in the context of injecting conductive materials into the heart and other organs, it is to be understood that this device could be used to deliver any type of medicine or liquid compound into any type of body.

While reference is often made to conduction pathways, it is to be understood that the modification to these pathways can include increasing their resistance or capacitance. This depends upon the material chosen to be injected into the body tissue. The term artificial conduction pathways or fields is to be understood to include increasing or decreasing conductance, resistance, or both, depending upon the material that is impregnated into the tissue.

While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. A method for altering the functioning of organs of the body, by altering and/or redirecting the body's naturally occurring electrical impulses, by injecting into the body tissue, materials with particular electrical properties, so as to create pathways, fields or patterns having different electrical properties, that include greater or less: conductance, resistance or capacitance or a combination of them, than the native tissue into which the said materials were injected.

2. The method of claim 1, wherein the altered functioning of the organs of the body is effected for the purpose of treating certain body disorders, for example, dysrhythmias of the heart including atrial fibrillation, AV block, SA block, reentry, refection, angina and pathological automaticity;

and also neurological disorders, such as migrane headaches; and for altering the transmission of electrical impulses through nerve pathways, for the treatment of paralysis and other nerve and muscular disorders.

* * * * *